US012551231B2

(12) United States Patent
Liu et al.

(10) Patent No.: US 12,551,231 B2
(45) Date of Patent: Feb. 17, 2026

(54) DRIVING DEVICE AND ROTARY GRINDING APPARATUS

(71) Applicant: SHANGHAI MICROPORT ROTAPACE MEDTECH CO., LTD., Shanghai (CN)

(72) Inventors: Peifeng Liu, Shanghai (CN); Xiaofei Ji, Shanghai (CN); Longfei Wang, Shanghai (CN); Jie Zhang, Shanghai (CN); Zhaohua Chang, Shanghai (CN)

(73) Assignee: SHANGHAI MICROPORT ROTAPACE MEDTECH CO., LTD., Shanghai (CN)

( * ) Notice: Subject to any disclaimer, the term of this patent is extended or adjusted under 35 U.S.C. 154(b) by 288 days.

(21) Appl. No.: 18/255,038

(22) PCT Filed: Nov. 1, 2021

(86) PCT No.: PCT/CN2021/127874
§ 371 (c)(1),
(2) Date: May 30, 2023

(87) PCT Pub. No.: WO2022/111221
PCT Pub. Date: Jun. 2, 2022

(65) Prior Publication Data

US 2024/0008892 A1 Jan. 11, 2024

(30) Foreign Application Priority Data

Nov. 30, 2020 (CN) ......................... 202011367918.1

(51) Int. Cl.
*A61B 17/3207* (2006.01)
*A61B 17/00* (2006.01)

(52) U.S. Cl.
CPC ................. *A61B 17/320758* (2013.01); *A61B 2017/00477* (2013.01); *A61B 2017/00539* (2013.01);
(Continued)

(58) Field of Classification Search
CPC .... A61B 17/320758; A61B 17/320725; A61B 17/32075; A61B 17/320783;
(Continued)

(56) References Cited

U.S. PATENT DOCUMENTS 4,146,030 A 3/1979 Holroyd
4,883,458 A 11/1989 Shiber
(Continued)

FOREIGN PATENT DOCUMENTS

CN 102056557 A 5/2011
CN 102131471 A 7/2011
(Continued)

OTHER PUBLICATIONS

Extended European Search Report issued for European Patent Application No. 21896722.2, dated Jul. 31, 2024, 8 pages.
(Continued)

*Primary Examiner* — Tuan V Nguyen
(74) *Attorney, Agent, or Firm* — HSML P.C.

(57) ABSTRACT

A driving device and a rotary grinding apparatus, comprising: a mounting sleeve (100), an accommodating chamber (101) being axially formed in the mounting sleeve (100), and the two ends of the mounting sleeve (100) in the axial direction being respectively a driving end (110) and a connecting end (120); a driving shaft (200), passing through the accommodating chamber (101) in the axial direction and rotatable about the axis; and a communication valve (300), provided in the accommodating chamber (101), an input channel (301) and a cooling channel (302) penetrating
(Continued)

through the communication valve (300) being formed inside the communication valve (300); one end of the input channel (301) being communicated with the cooling channel (302) and the other end being communicated with the outside to introduce a cooling medium; the cooling channel (302) being sleeved outside the driving shaft (200) in a clearance fit manner; and a first outlet (302*a*) and a second outlet (302*b*) being respectively formed on one side of the cooling channel (302) facing away from the driving end (110) and one side of the cooling channel (302) facing the driving end (110), and the first outlet (302*a*) being configured to output the cooling medium.

19 Claims, 3 Drawing Sheets

(52) U.S. Cl.
CPC ............... *A61B 2017/00544* (2013.01); *A61B 2217/007* (2013.01)

(58) Field of Classification Search
CPC .. A61B 17/32002; A61B 2017/320766; A61B 2017/320775
See application file for complete search history.

(56) References Cited

U.S. PATENT DOCUMENTS

| | | | | |
|---|---|---|---|---|
| 5,919,161 | A | 7/1999 | Hill, III et al. | |
| 2003/0028206 | A1 | 2/2003 | Shiber | |
| 2003/0114869 | A1* | 6/2003 | Nash | A61M 1/77 606/159 |
| 2005/0096649 | A1* | 5/2005 | Adams | A61B 18/149 606/171 |
| 2010/0036402 | A1 | 2/2010 | Hanson et al. | |
| 2011/0196402 | A1* | 8/2011 | Robertson | A61N 7/022 606/169 |
| 2019/0083127 | A1 | 3/2019 | Piippo Svendsen et al. | |
| 2020/0069328 | A1 | 3/2020 | Shiber | |
| 2020/0229844 | A1* | 7/2020 | Rawson | A61B 17/320758 |

FOREIGN PATENT DOCUMENTS

| | | | |
|---|---|---|---|
| CN | 201969471 | U | 9/2011 |
| CN | 102438535 | A | 5/2012 |
| CN | 104955406 | A | 9/2015 |
| CN | 104968285 | A | 10/2015 |
| CN | 107440763 | A | 12/2017 |
| CN | 109715092 | A | 5/2019 |
| CN | 209347149 | U | 9/2019 |
| CN | 111012448 | A | 4/2020 |
| CN | 211660953 | U | 10/2020 |
| CN | 211749912 | U | 10/2020 |
| CN | 112005042 | A | 11/2020 |
| CN | 112145746 | A | 12/2020 |
| DE | 1903618 | A1 | 9/1969 |
| DE | 3626684 | A1 | 2/1988 |
| GB | 1331802 | A | 9/1973 |
| WO | 9501754 | A1 | 1/1995 |
| WO | 2006126076 | A | 11/2006 |
| WO | 2010001405 | A1 | 1/2010 |
| WO | 2011005795 | A2 | 1/2011 |
| WO | 2018033920 | A1 | 2/2018 |
| WO | 2018075545 | A1 | 4/2018 |

OTHER PUBLICATIONS

International Search Report issued for International Patent Application No. PCT/CN2021/127874, Date of mailing: Feb. 7, 2022, 8 pages including English translation.
Written Opinion issued for International Patent Application No. PCT/CN2021/127874, Date of mailing: Feb. 7, 2022, 7 pages including partial English machine translation.
Office Action issued for Chinese Patent Application No. 202011367918.1, dated Jan. 7, 2021, 6 pages.
Search Report by patent search and consultation center of state intellectual property office, Chinese Patent Application No. 202011367918.1, dated Jan. 6, 2021, 5 pages.

* cited by examiner

DRIVING DEVICE AND ROTARY GRINDING APPARATUS

CROSS REFERENCE TO RELATED APPLICATION

This application claims priority to Chinese Patent Application No. 2020113679181, filed on Nov. 30, 2020, the contents of which is incorporated herein by reference in its entirety.

TECHNICAL FIELD

The present disclosure relates to the field of medical devices, in particular, to a driving device and a rotational atherectomy device.

BACKGROUND

A process of coronary atherectomy is mainly completed by a coronary rotational atherectomy device, which drives a diamond-coated atherectomy head through a flexible driving shaft to rotate coaxially, to grind and ablate coronary artery plaques into fine particles. The rotational atherectomy device includes a rotational atherectomy catheter system and a rotational atherectomy controller. The rotational atherectomy catheter system includes a rotational atherectomy propeller and a rotational atherectomy catheter. The rotational atherectomy propeller is mainly driven by a turbine motor, and controls the expansion and contraction of the rotational atherectomy head and secures a guiding wire. In addition, a prepared flushing fluid is transported from the outside to a distal end to continuously flush the rotational atherectomy head to cool it down. In this way, the rotational atherectomy head can be cooled and lubricated, the driving structure in the rotational atherectomy propeller can be cooled, coronary artery spasm can be prevented, and the diseased debris from the rotational atherectomy can be washed away.

During rotational atherectomy, when heat due to grinding and heat due to friction between flexible catheters causes the temperature of blood and vascular tissue to increase by more than 6° C., blood cell clusters may aggregate on cells of a vessel wall, resulting in dysfunction. Therefore, the flushing fluid must be injected in advance in time, with a flow rate being kept greater than 2 ml/min to ensure the cooling effect.

In the current flushing fluid and injection, generally, an infusion bag is connected to a liquid inlet pipe of a motor chamber of the rotational atherectomy propeller to realize the flow of the flushing fluid under gravity and external pressure. However, the starting or stopping of the flow of the flushing fluid is realized by loosening or squeezing rollers on an infusion tube matched with the infusion bag, which requires manual operation by medical personnel and is a passive operation function.

In addition, during a preoperative preparation process, it is necessary to manually confirm whether the flushing fluid can flow normally. A doctor will start the flushing fluid after the rotational atherectomy propeller is connected to the rotational atherectomy catheter, and confirm that there are drips of the flushing fluid under the motor chamber and at the distal end of the rotational atherectomy catheter at the same time, which means that an injection channel of the flushing fluid is normally unblocked.

In actual work, as a passive starting function, the operation of starting the flushing fluid may be ignored or may not be started in time during the surgery. Moreover, because whether the injection channel of the flushing fluid is unblocked and whether the flushing fluid is sufficient also require manual active confirmation, there is also the possibility of being ignored. How to prevent these mistakes from causing the temperature of the blood to rise, and resulting in blood cell coagulation to block blood vessels and complications such as slow blood flow and no-reflow, has become an urgent problem to be solved in current surgical operations.

SUMMARY

According to various embodiments of the present disclosure, a driving device and a rotational atherectomy device are provided.

A driving device includes:

a mounting sleeve, an accommodating cavity being formed in the mounting sleeve in an axial direction, and two ends of the mounting sleeve in the axial direction being a driving end and a connecting end respectively;

- a driving shaft, extending through the accommodating cavity in the axial direction, and being rotatable around an axis; and
- a communication valve, disposed in the accommodating cavity, wherein an input channel, and a cooling channel passing through the communication valve are formed in the communication valve; an end of the input channel communicates with the cooling channel, and the other end of the input channel communicates with outside to introduce a cooling medium; the cooling channel is sleeved on an outside of the driving shaft in a clearance fit; a first outlet and a second outlet are respectively formed on a side facing away from the driving end and on a side facing the driving end; and the first outlet is configured to output the cooling medium.

The above driving device has at least the following beneficial technical effects.

(1) When the driving device of the present application is in operation, once the cooling medium cannot enter the cooling channel normally due to various reasons (forgetting or failing to turn on the external supply device connected to the driving device in time, the channel being not connected due to a fault, and the insufficient cooling medium in the supply device), the heat generated by frequent contact of the high-speed rotating driving shaft with the wall surface of the cooling channel may cause the temperature of the communication valve to rise rapidly. When the driving shaft is operating at high speed and the cooling medium cannot enter the cooling channel normally, when the temperature of the communication valve rises to its heat deformation temperature, the communication valve can be deformed and bonded to the driving shaft as one piece, thereby directly hindering and blocking the driving shaft such that the driving shaft cannot rotate normally. In this way, it is possible to avoid the occurrence of damage to the patient's health due to vascular dysfunction caused by the driving shaft performing the rotational atherectomy on the blood vessel in the absence of cooling measures.

(2) By adopting the driving device of the embodiment, when the cooling function fails due to the operator forgetting or failing to turn on the supply device in time, the channel being not connected due to a fault, or the insufficient cooling medium in the supply device, etc., the temperature of the communication valve can quickly rise to lock the driving shaft such that the driving shaft cannot rotate normally, thereby preventing the blood vessels from being damaged by continuous rotational atherectomy in the absence of cooling measures.

In one of the embodiments, the communication valve is made of a material with a heat deformation temperature in a range from 130° C. to 270° C.

In one of the embodiments, the communication valve is made of a material with a heat deformation temperature in a range from 180° C. to 220° C.

In one of the embodiments, the communication valve is made of polyetherimide

In one of the embodiments, the cooling channel includes a second cooling channel and a first cooling channel that are connected in sequence in a direction from the driving end to the connecting end. A radial size of the first cooling channel is greater than a radial size of the second cooling channel. A radial size of a portion of the first cooling channel away from the second cooling channel is greater than a radial size of a portion of the first cooling channel approaching the second cooling channel.

In one of the embodiments, a difference between the radial size of the second cooling channel and a radial size of a driving shaft is in a range from 0.15 mm to 0.2 mm.

In one of the embodiments, the driving device further includes a guiding cover. The communication valve and the guiding cover are sequentially arranged in the accommodating cavity in a direction from the driving end to the connecting end, and are in sealing contact. An outlet channel through which the driving shaft passes is formed in the guiding cover. A side of the outlet channel facing away from the communication valve is configured to be connected to an output tube to output the cooling medium.

In one of the embodiments, a radial size of the outlet channel is less than a radial size of the cooling channel.

In one of the embodiments, a surface of the mounting sleeve defines an introducing hole communicating with the input channel to introduce the cooling medium from the outside.

In one of the embodiments, the driving device further includes an output tube. The output tube is connected to the first outlet, and sleeved on the driving shaft in a clearance fit.

In one of the embodiments, a discharge hole is defined on a surface of the mounting sleeve. The discharge hole communicates with the accommodating cavity through the second outlet, so as to discharge the cooling medium from the accommodating cavity.

In one of the embodiments, the driving device further includes a power component. The power component is disposed in the accommodating cavity and is closer to the driving end than the communication valve. The power component is connected to the driving shaft to drive the driving shaft to rotate In one of the embodiments, the power component includes:

a driving rotor, coaxially fixed to the driving shaft to synchronously drive the driving shaft to rotate relative to the mounting sleeve; and a slewing supporting structure, disposed between an outer surface of the driving rotor and an inner surface of the mounting sleeve, to provide support for a rotation of the driving rotor.

In one of the embodiments, the driving rotor includes a turbine rotor. A side wall of the mounting sleeve defines an air supply channel. The air supply channel is configured to connect the turbine rotor with an external air source to drive the turbine rotor to rotate.

In one of the embodiments, the slewing supporting structure includes slewing bearings disposed at both ends of the power component in an axial direction. An inner ring of the slewing bearing is sleeved on an outer peripheral surface of the driving rotor; and an outer ring of the slewing bearing is fixed on the inner surface of the mounting sleeve.

In one of the embodiments, the slewing supporting structure further includes a supporting sleeve. The supporting sleeve is filled between an outer surface of the slewing bearing and the inner surface of the mounting sleeve, to provide support for the slewing bearing.

In one of the embodiments, the power component is integrated in the driving device.

In one of the embodiments, the driving shaft extends out from the driving end, and is connected to external power device.

In one of the embodiments, a rotational atherectomy device includes a rotational atherectomy mechanism and the driving device as described above. The driving device is connected to the rotational atherectomy mechanism to drive the rotational atherectomy mechanism.

By adopting the rotational atherectomy device of the embodiment, when the driving shaft in the driving device is operating at high speed, if the function fails due to the operator forgetting or failing to turn on the supply device in time, the channel being not connected due to a fault, or the insufficient cooling medium in the supply device, etc., the temperature of the communication valve can quickly rise to the heat deformation temperature such that the communication valve is deformed and bonded to the driving shaft as one piece, which directly hinders and blocks the driving shaft so that the driving shaft cannot rotate normally, thereby preventing vascular dysfunction caused by continuous rotational atherectomy applied to blood vessels in the absence of cooling measures, and preventing damage to the patient's health.

In one of the embodiments, the driving device is detachably connected to the rotational atherectomy mechanism.

BRIEF DESCRIPTION OF THE DRAWINGS

In order to illustrate the technical solutions in the embodiments of the present application or prior art more clearly, the accompanying drawings used in the description of the embodiments or prior art will be briefly introduced below. Apparently, the accompanying drawings in the following description are only some embodiments of the present application. For those of ordinary skill in the art, other drawings can also be derived from these drawings without creative effort.

DETAILED DESCRIPTION OF THE EMBODIMENTS

Figure 1:
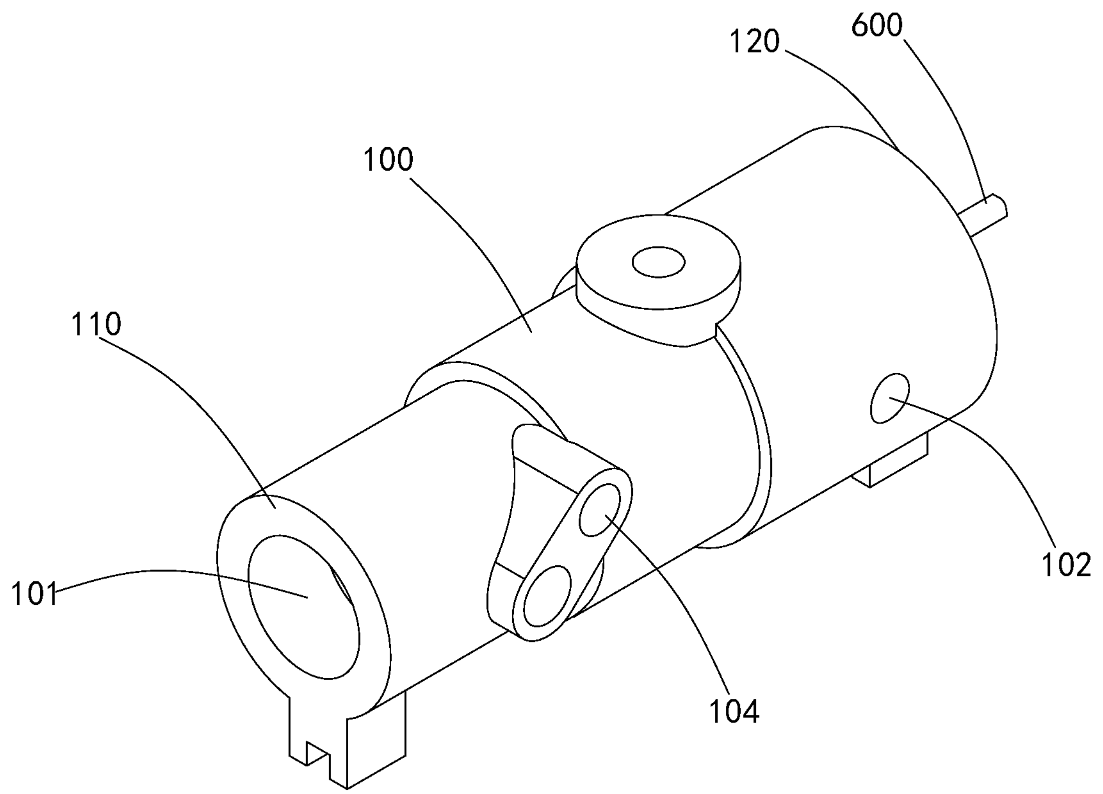
FIG. 1 is a perspective view of a driving device according to an embodiment of the present disclosure.

The present application will be further described below in conjunction with the accompanying drawings.

In order to facilitate the understanding of the present application, various embodiments defined by claims of the present application will be described more fully below with reference to the relevant drawings. Preferred embodiments of the present application are shown in the drawings, which include various specific details to facilitate that understanding, but these details should be regarded as exemplary only. However, the present application can be embodied in many different forms and is not limited to the embodiments described herein. Accordingly, those of ordinary skill in the art will recognize that changes and modifications of the various embodiments described herein can be made without departing from the scope of the present application as defined in the appended claims. In addition, descriptions of well-known functions and constructions may be omitted for clarity and conciseness.

It will be apparent to those skilled in the art that the following description of various embodiments of the present application is provided for the purpose of explanation only, and not for the purpose of limiting the present application as defined by the appended claims.

Throughout the specification and claims of the present application, the words "comprising" and "including" and variations of words such as "comprised" and "included" mean "including but not limited to", and are not intended (and will not be) to exclude other components, integers, or steps. Features, integers or characteristics described in conjunction with a particular aspect, embodiment or example of the present application are to be understood to be applicable to any other aspect, embodiment or example described herein unless incompatible therewith.

It should be understood that the singular forms "a", "an" and "the" include plural referents unless the context clearly states otherwise. The expressions "including" and/or "may include" used in the present application are intended to indicate the presence of corresponding functions, operations or elements, and are not intended to limit the existence of one or more functions, operations, and/or elements. In addition, in the present application, the terms "including" and/or "having" are intended to indicate the presence of characteristics, quantities, operations, elements, and components, or combinations thereof disclosed in the present application. Therefore, the terms "including" and/or "having" should be understood as that there are additional possibilities of one or more other characteristics, quantities, operations, elements and components, or combinations thereof.

In the present application, the expression "or" includes any or all combinations of words listed together. For example, "A or B" may include A or B, or may include both A and B.

It will be understood that when an element is referred to as being "fixed to" another element, it can be directly on another element, or intermediate elements may also be present; when an element is considered to be "connected" or "coupled" to another element, which can be directly or coupled to another element, or intermediate elements may also be present at the same time.

In order to describe the structural features of the present application more clearly, in the present application, "proximal end" and "distal end" are used as orientation words. "Proximal end" means an end close to the operator in the process of using the driving device or rotational atherectomy device. "Distal end" means an end away from the operator.

Unless otherwise defined, all technical and scientific terms used herein have the same meaning as commonly understood by one of ordinary skill in the technical field of the present application. It should also be understood that terms (such as those defined in commonly used dictionaries) should be interpreted as having consistent meanings in the relevant fields and in the context of this specification, and should not be interpreted in idealized or overly formalized meanings, unless expressly defined as such herein.

Figure 2:
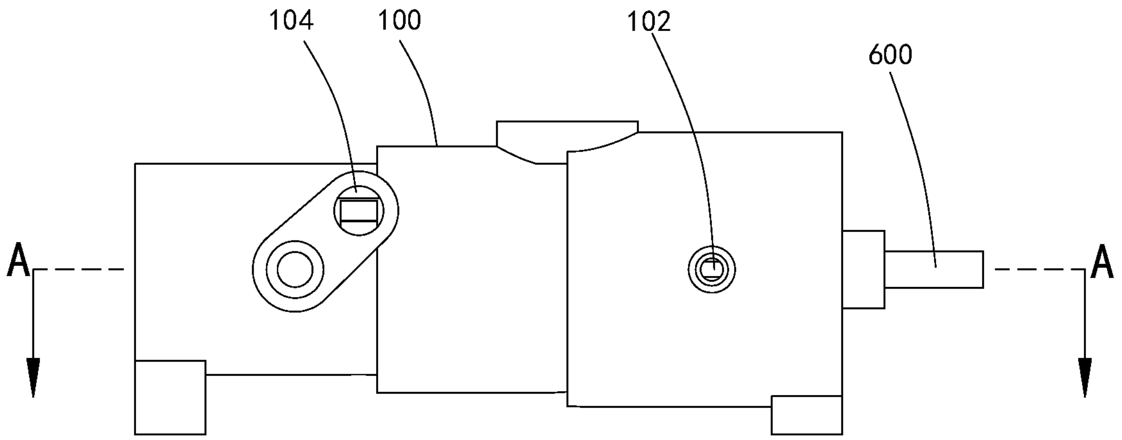
FIG. 2 is a front view of the driving device shown in FIG. 1.
Figure 3:
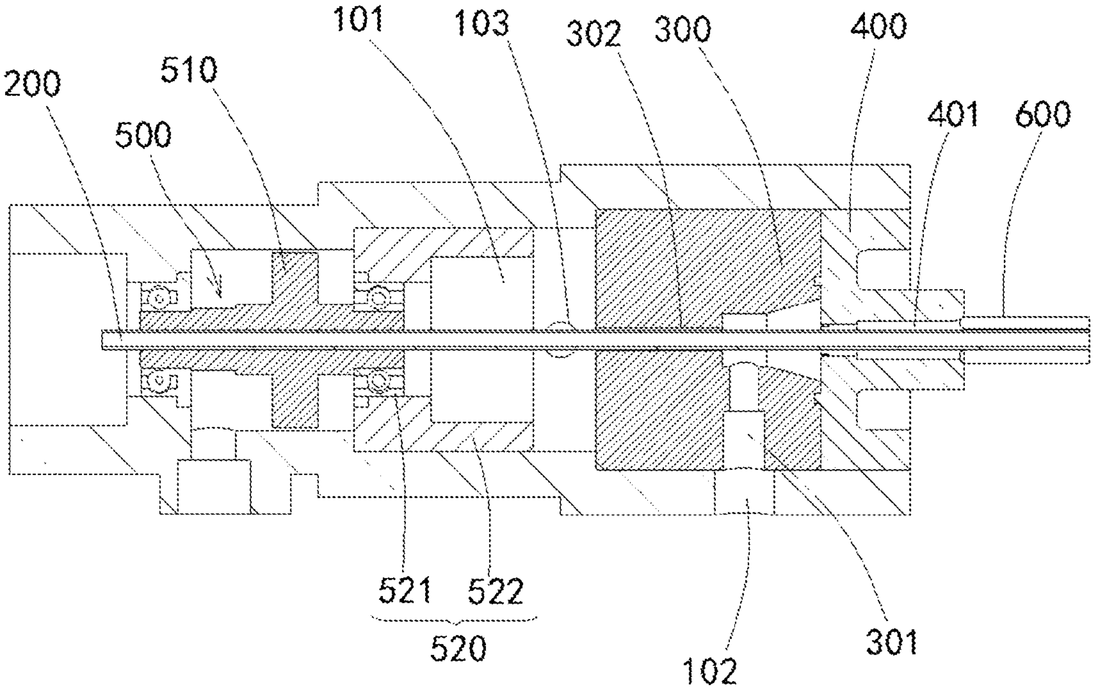
FIG. 3 is a cross-sectional view taken along a line A-A shown in FIG. 2.

As shown in FIGS. 1 to 3, in an embodiment of the present application, a driving device is provided, including a mounting sleeve 100, a driving shaft 200, and a communication valve 300.

An accommodating cavity 101 is formed in the mounting sleeve 100 in an axial direction, and the two ends of the mounting sleeve 100 in the axial direction are a driving end 110 and a connecting end 120 respectively.

The driving shaft 200 extends through the accommodating cavity 101 in the axial direction, and is rotatable around the axis.

The communication valve 300 is disposed in the accommodating cavity 101. An input channel 301, and a cooling channel 302 passing through the communication valve 300 in the axial direction are formed in the communication valve 300. An end of the input channel 301 communicates with the cooling channel 302, and the other end of the input channel 301 communicates with the outside to introduce a cooling medium. The cooling channel 302 is sleeved on the outside of the driving shaft 200 in a clearance fit. A first outlet **302*a* and a second outlet 302*b* are respectively formed on a side facing away from the driving end 110 and on a side facing the driving end 110, and are used to output the cooling medium from both ends of the cooling channel 302**.

It should be noted that, unless otherwise specified, "axial direction" in the text description herein refers to an axial direction of the mounting sleeve, and "axis" refers to an axis of the mounting sleeve.

Specifically, the driving shaft 200 is connected to an external driving device. An end of the driving shaft 200 protruding from the connecting end 120 is connected to a rotational atherectomy catheter and a rotational atherectomy head. A supply device for an external injection of cooling medium is connected to the input channel 301. In this way, the rotational atherectomy can be performed. As the cooling medium, physiological saline with different proportions, cooling gas or the like can be selected as required.

Referring to FIG. 1, in some embodiments, the driving device further includes an output tube 600. The output tube 600 is connected to the first outlet **302*a* and sleeved on the driving shaft 200** in a clearance fit.

In this embodiment, the output tube 600 can deliver the cooling medium to the rotational atherectomy catheter and the rotational atherectomy head at the distal end of the driving shaft 200 to cool down the blood vessels subjected to the rotational atherectomy. Moreover, the clearance fit between the output tube 600 and the driving shaft 200 can restrict the radial movement of the driving shaft 200 and prevent driving shaft 200 from freely swinging in the radial direction, thereby ensuring the normal transmission of the driving force.

During normal rotational atherectomy, the external supply device is turned on to inject the cooling medium to the rotational atherectomy catheter and the rotational atherectomy head at the end of the driving shaft 200 through the input channel 301, the cooling channel 302, and the output tube 600. The rotational atherectomy catheter and the rotational atherectomy head at the end of the driving shaft 200 extend into the inside of the blood vessel of the human body, and then, the driving shaft 200, the rotational atherectomy catheter, and the rotational atherectomy head are driven to rotate by starting the driving device. The rotational atherectomy head grinds and ablates coronary artery plaques into fine particles, and the cooling medium can cool down the blood vessels at the rotational atherectomy site and wash away the debris of vascular lesions from the rotational atherectomy. During this process, since the driving shaft 200 itself has a large length and low rigidity, so that the driving shaft 200 has a certain bending arc. During the rotation process of the driving shaft 200, the driving shaft 200 may swing in the radial direction, which may cause the driving shaft 200 to contact a wall surface of the cooling channel 302. Since the high-speed rotation speed of the driving shaft 200 in the rotational atherectomy is generally in a range from 6 wRPM to 12 wRPM, up to about 20 wRPM, during the high-speed rotation, the frequent contact between the driving shaft 200 and the wall surface of the cooling channel 302 is capable of generating a lot of heat, which may cause the communication valve 300 to heat up. Therefore, it is necessary to inject the cooling medium into the cooling channel 302. The cooling medium entering the cooling channel 302 absorbs heat, and flows out from the first outlet 302*a* and the second outlet 302*b* simultaneously, so as to cool down the communication valve 300. The cooling medium enters the accommodating cavity 101 after flowing out from the second outlet 302*b*, and can flow out from a surface of the mounting sleeve 100, or from the driving end 110 or the connecting end 120. In this way, the temperature of the communication valve 300 can be continuously lowered by continuously inputting the cooling medium into the cooling channel 302.

Once the cooling medium cannot enter the cooling channel 302 normally due to various reasons (forgetting or failing to turn on the supply device in time, the channel being not connected due to a fault, and the insufficient cooling medium in the supply device), the heat generated by frequent contact of the high-speed rotating driving shaft 200 with the wall surface of the cooling channel 302 may cause the temperature of the communication valve 300 to rise rapidly and greatly (up to 300° C. or higher). In case that the driving shaft 200 is operating at high speed and the cooling medium cannot enter the cooling channel 302 normally, when the temperature of the communication valve 300 rises to its heat deformation temperature, the communication valve 300 can be deformed and bonded to the driving shaft 200 as one piece, thereby directly hindering and blocking the driving shaft 200 such that the driving shaft 200 cannot rotate normally. In this way, it is possible to avoid the occurrence of damage to the patient's health due to vascular dysfunction caused by the driving shaft performing the rotational atherectomy on the blood vessel in the absence of cooling measures.

By using the driving device according to this embodiment, when the cooling function fails due to the operator forgetting or failing to turn on the supply device in time, the channel being not connected due to a fault, or the insufficient cooling medium in the supply device, etc., the communication valve 300 can quickly heat up to lock the driving shaft 200, to stop the rotation of the driving shaft 200, thereby preventing the blood vessel from being damaged due to rotational atherectomy in the absence of cooling measures.

It should be noted that, during the above-mentioned process of performing the rotational atherectomy in blood vessels, since the internal pressure of the human blood vessels is lower than the external atmospheric pressure, the existence of the pressure difference can facilitate the tendency of the cooling medium to mainly flow out from the first outlet 302*a*, and then to flow towards the distal end of the driving shaft 200, i.e., into the blood vessel.

In the above-mentioned embodiments, the communication valve 300 is deformed due to temperature rise and bonded to the driving shaft 200 to block the normal operation of the driving shaft 200. It can be understood that in some other embodiments, when the temperature rise is sensed by the outside world (for example, combined with the operator's tactile perception, infrared temperature monitor monitoring, etc.), the operator knows that the cooling is abnormal, and then turns down the driving device immediately. In this way, it can also prevent vascular dysfunction caused by rotational atherectomy applied to blood vessels in the absence of cooling measures, and which is not limited herein.

In some embodiments, the communication valve 300 is made of a material with a heat deformation temperature in a range from 130° C. to 270° C. Specifically, the communication valve 300 can be made of a material with a suitable preset heat deformation temperature which may be selected according to actual surgical needs and the specific material of the driving shaft in the driving device. When the heat deformation temperature of the communication valve 300 is stable and within a reasonable range, the communication valve 300 can be deformed and lock the driving shaft 200 in time when the cooling function fails, so as to prevent the driving device from heating up in time and avoid damage to blood vessels. In addition, under the condition that necessary cooling measures are provided, the small increase in temperature of the communication valve 300 will not affect the normal rotation of the driving shaft and the normal use of the driving device. According to different needs, the communication valve 300 can be made of materials with different heat deformation temperatures which may be selected within the above range, so as to flexibly meet more usage needs. Furthermore, the communication valve 300 can be made of a material with a heat deformation temperature in a range from 180° C. to 220° C., which can further improve the reliability of the communication valve 300 and ensure that the driving shaft 200 is locked within a suitable temperature range.

In some embodiments, the communication valve 300 is made of polyetherimide.

Polyetherimide is an amber transparent solid with excellent mechanical properties and wear resistance, and with a heat deformation temperature in a range from 198° C. to 208° C. Therefore, the communication valve 300 made of polyetherimide can be used for a long time at an operating temperature in a range from −160° C. to 180° C. In case of the absence of cooling medium injection, the internal temperature of the communication valve 300 will increase significantly as the friction time increases. When the internal temperature of the communication valve 300 exceeds the heat deformation temperature of the communication valve 300 such that the communication valve 300 is deformed, even when the communication valve 300 melts due to the internal temperature being greater than 300° C., the deformation or melting of the communication valve 300 can hinder and block the driving shaft 200 such that the driving shaft 200 cannot rotate normally, to avoid severe injury to the patient due to obvious temperature rise caused by performing surgery when an infusion bag is forgotten to be turned on or the cooling medium in the infusion bag is insufficient. In addition, since the polyetherimide has a certain tolerance to temperature, the polyetherimide may not melt and cause the driving shaft 200 to be locked when the temperature rises only slightly (for example, rises by 10° C. to 50° C.). Therefore, the communication valve 300 made of polyetherimide may not affect the normal rotation of the driving shaft and the normal use of the driving device when necessary cooling measures are available, and has good stability and long service life.

When the temperature of the communication valve 300 in this embodiment rises to the heat deformation temperature, the communication valve 300 can be deformed and bonded to the driving shaft 200 as one piece, thereby directly hindering and locking the driving shaft 200 to stop the rotation of the driving shaft 200, thereby preventing the injury to the blood vessels due to continuous rotational atherectomy in the absence of cooling measures, which is safer and can prevent serious medical accidents caused by human errors.

In some other embodiments, the communication valve 300 can also be made of other materials with a heat deformation temperature in a range from 130° C. to 270° C. The communication valve 300 made of such materials can lock the driving shaft 200 in the absence of cooling measures to prevent damage, and may not affect the normal usage of the driving device when the temperature rises slightly with available reasonable cooling measures, and which is no limited herein.

Figure 4:
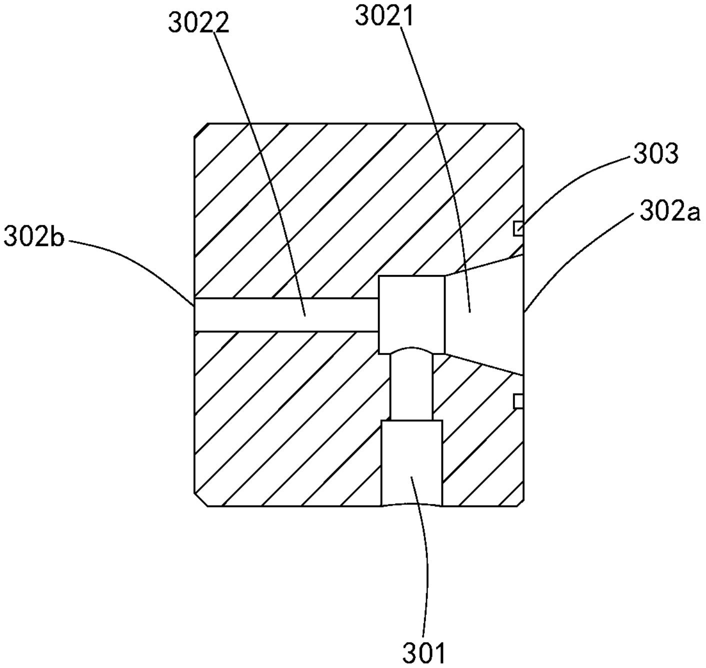
FIG. 4 is an enlarged view of a communication valve shown in FIG. 3.

Referring to FIG. 4, in some embodiments, the cooling channel 302 includes a second cooling channel 3022 and a first cooling channel 3021 that are connected in sequence in a direction from the driving end 110 to the connecting end 120. A radial size of the first cooling channel 3021 is greater than a radial size of the second cooling channel 3022, and a radial size of a portion of the first cooling channel 3021 away from the second cooling channel 3022 is greater than a radial size of a portion of the first cooling channel 3021 approaching the second cooling channel 3022.

Specifically, since the radial size of the first cooling channel 3021 is greater than the radial size of the second cooling channel 3022, the radial size of the first cooling channel 3021 has a tendency to increase in a direction from approaching the second cooling channel 3022 to being away from the second cooling channel 3022. Therefore, the first cooling channel 3021 can form a shape similar to a bell mouth, that is, a gap between the first cooling channel 3021 and the driving shaft 200 gradually increases in this direction, which is beneficial to facilitate the tendency of most of the cooling medium to flow towards the first outlet 302*a* and be delivered to the rotational atherectomy head at the distal end.

In some embodiments, a difference between the radial size of the second cooling channel 3022 and the radial size of the driving shaft 200 is in a range from 0.15 mm to 0.2 mm.

Specifically, after adopting this size difference, the second cooling channel 3022 may not affect the flow of the cooling medium towards the first cooling channel 3021. In addition, the gap between the second cooling channel 3022 and the driving shaft 200 is small, which can restrict the radial movement of the driving shaft 200, and prevent the driving shaft 200 from freely swinging in the radial direction, thereby ensuring the normal transmission of the driving force.

Referring to FIG. 3, in some embodiments, the driving device further includes a guiding cover 400. The communication valve 300 and the guiding cover 400 are sequentially arranged in the accommodating cavity 101 in the direction from the driving end 110 to the connecting end 120, and are in sealing contact. An outlet channel 401 through which the driving shaft 200 passes is formed in the guiding cover 400. A side of the outlet channel 401 facing away from the communication valve 300 is used to be connected to the output tube 600 to output the cooling medium.

Figure 5:
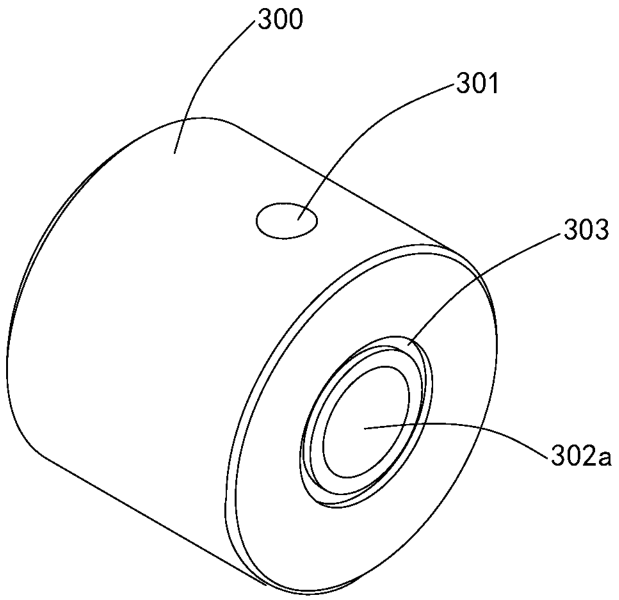
FIG. 5 is a perspective view of the communication valve.

Specifically, as shown in FIG. 5, a fixing groove 303 is provided on an end surface of the communication valve 300 facing the guiding cover 400. Inserting a sealing ring into the fixing groove 303 can realize the sealing connection between the guiding cover 400 and the communication valve 300. The sealing contact between the guiding cover 400 and the communication valve 300 can prevent the cooling medium from overflowing from between the guiding cover 400 and the communication valve 300. In this embodiment, the output tube 600 can be directly connected to the outlet channel 401 of the guiding cover 400, so that the output tube 600 can communicate with the cooling channel 302 by using the guiding cover 400. The provided guiding cover 400 facilitates the cooperative mounting of the first outlet 302*a* and the output tube 600.

Further, a radial size of the outlet channel 401 is less than a maximum radial size of the first cooling channel 3021. Since the radial size of the outlet channel 401 is less than the maximum radial size of the first cooling channel 3021, when the cooling medium enters the smaller-sized outlet channel 401, the flow rate may be significantly increased under the condition of constant quantity of flow, thereby improving the cooling effect on the rotational atherectomy catheter and the rotational atherectomy head at the distal end.

Referring to FIG. 1, in some embodiments, a side wall of the mounting sleeve 100 defines an introducing hole 102 communicating with the input channel 301 to introduce the cooling medium from the outside.

Specifically, after the supply device is connected to the introducing hole 102, the cooling medium in the supply device can flow into the input channel 301 through the introducing hole 102, and then flow into the cooling channel 302 to play a cooling effect.

It can be understood that, in some other embodiments, the input channel 301 may be connected to external supply device through a structure such as a delivery tube, and which is not specifically limited here.

Referring to FIG. 3, in some embodiments, a discharge hole 103 is defined on the side wall of the mounting sleeve 100. The discharge hole 103 communicates with the accommodating cavity 101 through the second outlet 302*b*, so as to discharge the cooling medium from the accommodating cavity.

Specifically, after flowing out from the second outlet 302*b* and entering the accommodating cavity 101, the cooling medium can flow out from the discharge hole 103 on the side wall of the mounting sleeve 100, thus preventing the cooling medium from accumulating inside the accommodating cavity 101 and ensuring continuous inputting of the cooling medium into the cooling channel 302 to cool down the communication valve 300. Certainly, in other embodiments, the accommodating cavity 101 may be directly disposed to extend through the driving device, and the cooling medium flows out directly from the driving end 110 and the connecting end 120.

Referring to FIG. 3, in some embodiments, the driving device further includes a power component 500. The power component 500 is disposed in the accommodating cavity 101 and is closer to the driving end 110 than the communication valve 300. The power component 500 is connected to the driving shaft 200 to drive the driving shaft 200 to rotate. The power component 500 is integrated in the driving device, that is, the power component 500 and the driving device are designed in one piece, which can save space and simplify the overall structural design.

It can be understood that, in some other embodiments, the driving shaft 200 can extend out from the driving end 110 and be connected to external power device. Therefore, starting an external power device can also drive the driving shaft 200 to rotate, and which is not limited herein.

Continuing to refer to FIG. 3, in some embodiments, the power component 500 includes a driving rotor 510 and a slewing supporting structure 520.

The driving rotor 510 is coaxially fixed to the driving shaft 200 to synchronously drive the driving shaft 200 to rotate relative to the mounting sleeve 100.

The slewing supporting structure 520 is disposed between an outer surface of the driving rotor 510 and an inner surface of the mounting sleeve 100, to provide support for the rotation of the driving rotor 510.

Specifically, the rotation of the driving rotor 510 can cause the driving shaft 200 to rotate relative to the mounting sleeve 100, and the slewing supporting structure 520 is disposed between the outer surface of the driving rotor 510 and the inner surface of the mounting sleeve 100, so as to rotatably connected the driving rotor 510 with the mounting sleeve 100. In this way, when the driving rotor 510 rotates, the position of the slewing supporting structure 520 is stable, which can provide support for the rotation of the driving rotor 510, and avoid displacement of the driving rotor 510 inside the accommodating cavity during its rotation.

In some embodiments, the driving rotor 510 includes a turbine rotor. The side wall of the mounting sleeve 100 defines an air supply channel 104. The air supply channel 104 is used to connect the turbine rotor with an external air source to drive the turbine rotor to rotate.

Specifically, an external air source is connected to the air supply channel 104. The external air source blows high-pressure air to the turbine rotor to drive the turbine rotor to rotate, thereby driving the driving shaft 200 to rotate at a high speed. The driving shaft 200 simultaneously drives the rotational atherectomy catheter and the rotational atherectomy head at the distal end to rotate synchronously at a high speed, thereby grinding and ablating coronary artery plaques into fine particles.

The structure and driving method of the turbine rotor in this embodiment are relatively simple, and high-pressure airflow is used as a power source, which is green and energy-saving and does not generate excessive heat due to operation.

Referring to FIG. 3, in some embodiments, the slewing supporting structure 520 includes slewing bearings 521 disposed at both ends of the power component 500 in an axial direction. An inner ring of the slewing bearing 521 is sleeved on an outer peripheral surface of the driving rotor 510. An outer ring of the slewing bearing 521 is fixed on an inner surface of the mounting sleeve 100.

Specifically, the slewing bearing 521 can bear large axial and radial loads at the same time, and can provide stable support for the driving rotor 510. The slewing bearing 521 is disposed at both ends of the power component 500 in the axial direction, and which can support the drive rotor 510 in a balanced manner.

In some cases, a radial size in a direction perpendicular to the axial direction of the accommodating cavity 101 is relatively large. In this case, the outer ring of the slewing bearing 521 cannot be directly connected and fixed to the inner surface of the accommodating cavity 101. Referring to FIG. 3, in some embodiments, the slewing supporting structure 520 further includes a supporting sleeve 522. The supporting sleeve 522 is filled between a surface of the outer ring of the slewing bearing 521 and the inner surface of the mounting sleeve 100, to provide support for the slewing bearing 521.

The supporting sleeve 522 in this embodiment effectively bridges the gap between the outer surface of the slewing bearing 521 and the inner surface of the accommodating cavity 101, and is fixedly connected to the outer surface of the slewing bearing 521 and the inner surface of the mounting sleeve 100 respectively, so that the slewing bearing 521 is firmly connected with the mounting sleeve 100, avoiding the separation of the outer surface of the slewing bearing 521 from the inner surface of the mounting sleeve 100 during the high rotation of the driving shaft 200, thereby avoiding support failure and serious safety accidents.

The present application further provides a rotational atherectomy device, which includes a rotational atherectomy mechanism and the driving device as described above. The connecting end of the driving device is connected to the rotational atherectomy mechanism to drive the rotational atherectomy mechanism. The rotational atherectomy mechanism generally includes a rotational atherectomy catheter and a rotational atherectomy head. A surface of the rotational atherectomy head is provided with an abrasive layer for grinding lesion plaques in a living body. In a preferred embodiment, during specific use, the driving device is detachably connected to the rotational atherectomy mechanism. In this way, when the communication valve in the rotational atherectomy mechanism is locked with the driving shaft, only the driving device needs to be replaced to continue the rotational atherectomy without replacing the entire rotational atherectomy device, thus avoiding the need to withdraw the rotational atherectomy mechanism from the patient's body and replace it with a new rotational atherectomy device and re-insert the new rotational atherectomy device into the body, which not only reduces the loss cost caused by improper operation, but also shortens the operation time and reduces the injury to the patient. The rotational atherectomy can be performed by connecting the external supply device for injecting the cooling medium to the input channel 301 of the driving device.

By adopting the driving device and the rotational atherectomy device of the present application, when the cooling function fails due to the operator forgetting or failing to turn on the supply device in time, the channel being not connected due to a fault, or the insufficient cooling medium in the supply device, etc., the temperature of the communication valve can quickly rise to the heat deformation temperature, such that the communication valve is deformed and bonded to the driving shaft as one piece, thereby directly hindering and locking the driving shaft such that the driving shaft cannot rotate normally, thereby preventing vascular dysfunction caused by continuous rotational atherectomy applied to blood vessels in the absence of cooling measures, and preventing damage to the patient's health.

In the above description, although expressions such as "first" and "second" may be used to describe the respective elements of the present application, they are not intended to limit the corresponding elements. For example, the above expressions are not intended to limit the order or importance of corresponding elements. The above expressions are used to distinguish one component from another.

The terms used herein in the description of the present application are for the purpose of describing specific embodiments only, and are not intended to limit the present application. A singular expression includes a plural expression, unless there is a significant difference in context or scheme therebetween.

The above descriptions are only exemplary implementations of the present application, and are not intended to limit the protection scope of the present application, which is subjected to the appended claims. For example, the driving device of the present application is not limited to be connected to the rotational atherectomy mechanism to form the rotational atherectomy device, but can also be connected and cooperated with medical devices with rotation shafts such as suction rotational cutting catheters, dental drills, or orthopedic drills, to form various types of medical devices, and perform different types of medical treatments or plastic surgery.

Those skilled in the art can understand that the various technical features of the above-mentioned embodiments can be correspondingly omitted, added or combined in any manner, and for the sake of concise description, all possible combinations of the various technical features in the above-mentioned embodiments are not described. However, as long as there is no contradiction in the combination of these technical features, and the simple variants that can be conceived by those skilled in the art and the solutions obtained by making adaptive and functional structural variants to the existing technology should be considered as being fallen within the scope described in present application.

The above-mentioned embodiments only illustrate several implementations of the present application, and the description thereof is relatively specific and detailed, but should not be construed as limiting the scope of the patent application. It should be noted that although the present application has been shown and described with reference to various embodiments, various modifications and improvements in form and details may be made by those of ordinary skill in the art without departing from the concept of the present application, and without departing from the scope of the present application defined by the appended claims, all of which belong to the protection scope of the present application. Therefore, the protection scope of the patent application should be subjected to the appended claims.

What is claimed is:

1. A driving device, comprising:

a mounting sleeve, an accommodating cavity being formed in the mounting sleeve in an axial direction, and two ends of the mounting sleeve in the axial direction being a driving end and a connecting end respectively;

a driving shaft extending through the accommodating cavity in the axial direction, and being rotatable around an axis; and a communication valve disposed in the accommodating cavity, wherein an input channel, and a cooling channel passing through the communication valve are formed in the communication valve; an end of the input channel communicates with the cooling channel, and the other end of the input channel communicates with outside to introduce a cooling medium; the cooling channel is sleeved on an outside of the driving shaft in a clearance fit; a first outlet and a second outlet are respectively formed on a side facing away from the driving end and on a side facing the driving end; and the first outlet is configured to output the cooling medium;

wherein the communication valve is made of a material with a heat deformation temperature in a range from 130° C. to 270° C.

2. The driving device according to claim 1, wherein the communication valve is made of a material with a heat deformation temperature in a range from 180° C. to 220° C.

3. The driving device according to claim 1, wherein the communication valve is made of polyetherimide.

4. The driving device according to claim 1, wherein the cooling channel comprises a second cooling channel and a first cooling channel that are connected in sequence in a direction from the driving end to the connecting end; a radial size of the first cooling channel is greater than a radial size of the second cooling channel, and a radial size of a portion of the first cooling channel away from the second cooling channel is greater than a radial size of a portion of the first cooling channel approaching the second cooling channel.

5. The driving device according to claim 4, wherein a difference between the radial size of the second cooling channel and a radial size of a driving shaft is in a range from 0.15 mm to 0.2 mm.

6. The driving device according to claim 1, further comprising a guiding cover, wherein the communication valve and the guiding cover are sequentially arranged in the accommodating cavity in a direction from the driving end to the connecting end, and are in sealing contact; an outlet channel through which the driving shaft passes is formed in the guiding cover; and a side of the outlet channel facing away from the communication valve is configured to be connected to an output tube to output the cooling medium.

7. The driving device according to claim 6, wherein a radial size of the outlet channel is less than a radial size of the cooling channel.

8. The driving device according to claim 1, wherein a surface of the mounting sleeve defines an introducing hole communicating with the input channel to introduce the cooling medium from the outside.

9. The driving device according to claim 1, further comprising an output tube, wherein the output tube is connected to the first outlet, and sleeved on the driving shaft in a clearance fit.

10. The driving device according to claim 1, wherein the driving shaft extends out from the driving end, and is connected to external power device.

11. A rotational atherectomy device, comprising:

a rotational atherectomy mechanism; and the driving device according to claim 1;

wherein the driving device is connected to the rotational atherectomy mechanism to drive the rotational atherectomy mechanism.

12. The rotational atherectomy device according to claim 11, wherein the driving device is detachably connected to the rotational atherectomy mechanism.

13. A driving device, comprising:

a mounting sleeve, an accommodating cavity being formed in the mounting sleeve in an axial direction, and two ends of the mounting sleeve in the axial direction being a driving end and a connecting end respectively;

a driving shaft extending through the accommodating cavity in the axial direction, and being rotatable around an axis; and a communication valve disposed in the accommodating cavity, wherein an input channel, and a cooling channel passing through the communication valve are formed in the communication valve; an end of the input channel communicates with the cooling channel, and the other end of the input channel communicates with outside to introduce a cooling medium; the cooling channel is sleeved on an outside of the driving shaft in a clearance fit; a first outlet and a second outlet are respectively formed on a side facing away from the driving end and on a side facing the driving end; and the first outlet is configured to output the cooling medium;

wherein a discharge hole is defined on a surface of the mounting sleeve; and the discharge hole communicates with the accommodating cavity through the second outlet, so as to discharge the cooling medium from the accommodating cavity.

14. A driving device, comprising:

a mounting sleeve, an accommodating cavity being formed in the mounting sleeve in an axial direction, and two ends of the mounting sleeve in the axial direction being a driving end and a connecting end respectively;

a driving shaft extending through the accommodating cavity in the axial direction, and being rotatable around an axis;

a communication valve disposed in the accommodating cavity, wherein an input channel, and a cooling channel passing through the communication valve are formed in the communication valve; an end of the input channel communicates with the cooling channel, and the other end of the input channel communicates with outside to introduce a cooling medium; the cooling channel is sleeved on an outside of the driving shaft in a clearance fit; a first outlet and a second outlet are respectively formed on a side facing away from the driving end and on a side facing the driving end; and the first outlet is configured to output the cooling medium; and a power component, wherein the power component is disposed in the accommodating cavity and is closer to the driving end than the communication valve; and the power component is connected to the driving shaft to drive the driving shaft to rotate.

15. The driving device according to claim 14, wherein the power component comprises:

a driving rotor coaxially fixed to the driving shaft to synchronously drive the driving shaft to rotate relative to the mounting sleeve; and a slewing supporting structure disposed between an outer surface of the driving rotor and an inner surface of the mounting sleeve, to provide support for a rotation of the driving rotor.

16. The driving device according to claim 15, wherein the driving rotor comprises a turbine rotor; a side wall of the mounting sleeve defines an air supply channel; and the air supply channel is configured to connect the turbine rotor with an external air source to drive the turbine rotor to rotate.

17. The driving device according to claim 15, wherein the slewing supporting structure comprises slewing bearings disposed at both ends of the power component in an axial direction; an inner ring of the slewing bearing is sleeved on an outer peripheral surface of the driving rotor; and an outer ring of the slewing bearing is fixed on the inner surface of the mounting sleeve.

18. The driving device according to claim 17, wherein the slewing supporting structure further comprises a supporting sleeve; the supporting sleeve is filled between an outer surface of the slewing bearing and the inner surface of the mounting sleeve, to provide support for the slewing bearing.

19. The driving device according to claim 14, wherein the power component is integrated in the driving device.

* * * * *